United States Patent
Tapadar et al.

(10) Patent No.: US 10,910,108 B2
(45) Date of Patent: Feb. 2, 2021

(54) INDICATOR FOR PROBABLE INHERITANCE OF GENETIC DISEASE

(71) Applicant: CERNER INNOVATION, INC., Kansas City, KS (US)

(72) Inventors: Soumen Tapadar, Karnataka (IN); Leena Verma, Karnataka (IN)

(73) Assignee: CERNER INNOVATION, INC., Kansas City, KS (US)

( * ) Notice: Subject to any disclaimer, the term of this patent is extended or adjusted under 35 U.S.C. 154(b) by 701 days.

(21) Appl. No.: 15/393,817

(22) Filed: Dec. 29, 2016

(65) Prior Publication Data

US 2018/0189456 A1 Jul. 5, 2018

(51) Int. Cl.

| | | |
|---|---|---|
| *G06F 21/62* | (2013.01) | |
| *G06Q 50/00* | (2012.01) | |
| *G16H 50/30* | (2018.01) | |
| *G16H 50/20* | (2018.01) | |
| *G16H 10/60* | (2018.01) | |
| *G16H 40/67* | (2018.01) | |
| *G16H 40/63* | (2018.01) | |

(52) U.S. Cl.
CPC ............ *G16H 50/30* (2018.01); *G16H 10/60* (2018.01); *G16H 40/63* (2018.01); *G16H 40/67* (2018.01); *G16H 50/20* (2018.01)

(58) Field of Classification Search
CPC ........ G16H 50/30; G16H 10/60; G16H 50/20; G16H 50/70; G16H 10/20; G16H 50/50; G16H 40/67; G16H 15/00; G16H 40/63; G16H 40/20; G16H 30/20; G16H 30/40; G16H 40/60; G16B 20/00; A61B 5/0002; A61B 5/11; G06Q 50/24; G06Q 10/10; G06Q 10/06; G06F 19/00; G06F 19/3418; G06F 19/325; G06F 19/3456; G06F 3/04817; G06F 3/04842; G06F 19/321; G06F 19/3481; G06F 19/3468

See application file for complete search history.

(56) References Cited

U.S. PATENT DOCUMENTS

| | | | |
|---|---|---|---|
| 9,171,285 B2 * | 10/2015 | Greene | ................ G06Q 10/087 |
| 2009/0018863 A1 * | 1/2009 | Yoon | ..................... G06Q 40/08 |
| | | | 705/2 |
| 2017/0242963 A1 * | 8/2017 | Cohen | ................... G06F 19/321 |

* cited by examiner

*Primary Examiner* — Maroun P Kanaan

(74) *Attorney, Agent, or Firm* — Shook, Hardy & Bacon, L.L.P.

(57) ABSTRACT

Systems, methods and computer-readable media are provided for identification of patients or family member having genetic disease or probable genetic disease. During or after registration of a patient, parents, grandparents, or siblings of the patient are identified. If it is determined that one of the patient or the parents, grandparents, or siblings of the patient has been assigned with a diagnosis indicating a genetic disease, an alert for genetic disease or probable genetic disease for the patient or family member of the patient is provided. A clinician is then prompted to confirm or rule out the patient or family member inheriting the disease.

21 Claims, 12 Drawing Sheets

INDICATOR FOR PROBABLE INHERITANCE OF GENETIC DISEASE

BACKGROUND

Many diseases can be passed along from one family member to another. These diseases are often due to changes or mutations in a gene that is inherited from one or both parents. However, these diseases are often misdiagnosed due to incomplete medical records or a lack of knowledge by a patient that a possible genetic disease may have been passed to the patient. As a result, the opportunity for early diagnosis and treatment may be missed and the health of the patient may deteriorate.

SUMMARY

Systems, methods and computer-readable media are provided for the identification of patients having a probable inheritance of a genetic disease. In particular, embodiments of the invention are directed to identifying parents, grandparents, or siblings of a patient collected during registration of the patient. If it is determined that one of the patient or the parents, grandparents, or siblings of the patient has been assigned with a diagnosis indicating a genetic disease, an alert for a genetic disease or probable genetic disease for patient or family member of the patient is provided. The alert includes providing a genetic disease or probable genetic disease icon in an electronic health record of the patient or family member of the patient.

In some embodiments, a clinician is prompted to confirm or rule out the patient or the parents, grandparents, or siblings of the patient having the genetic disease. Upon receiving an indication that the patient or family member has been ruled out as having the genetic disease, a record of the patient or family member in the healthcare system is updated with no alerts indicating the patient or family member of the patient does not have genetic disease or probable genetic disease. This includes removing the genetic disease icon or probable genetic disease icon from the electronic health record of the patient or family member of the patient. In contrast, upon receiving an indication that the patient or family member has been confirmed as having the genetic disease, the probable genetic disease icon is replaced with a genetic disease icon in the electronic health record of the patient or family member indicating the patient or family member has the genetic disease.

In this way, embodiments of the invention facilitate the early diagnosis and treatment of genetic diseases.

BRIEF DESCRIPTION OF THE DRAWINGS

The present invention is described in detail below with reference to the attached drawing figures, wherein:

Figure 5:
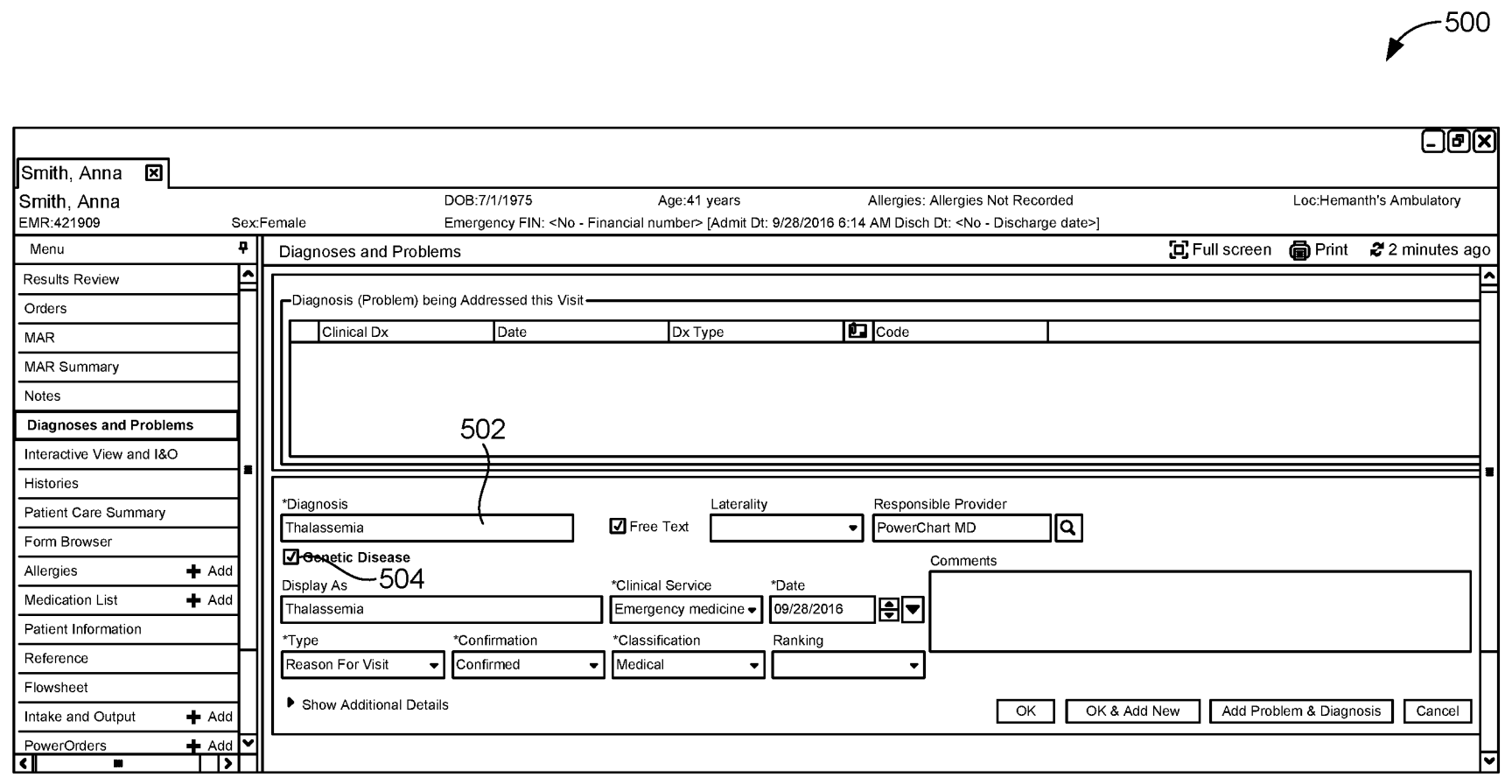

FIGS. 5-12 are exemplary graphical user interfaces illustrating identification of patients having genetic disease and family member of the patient with probable genetic disease, in accordance with embodiments of the present invention.

DETAILED DESCRIPTION

Figure 1:
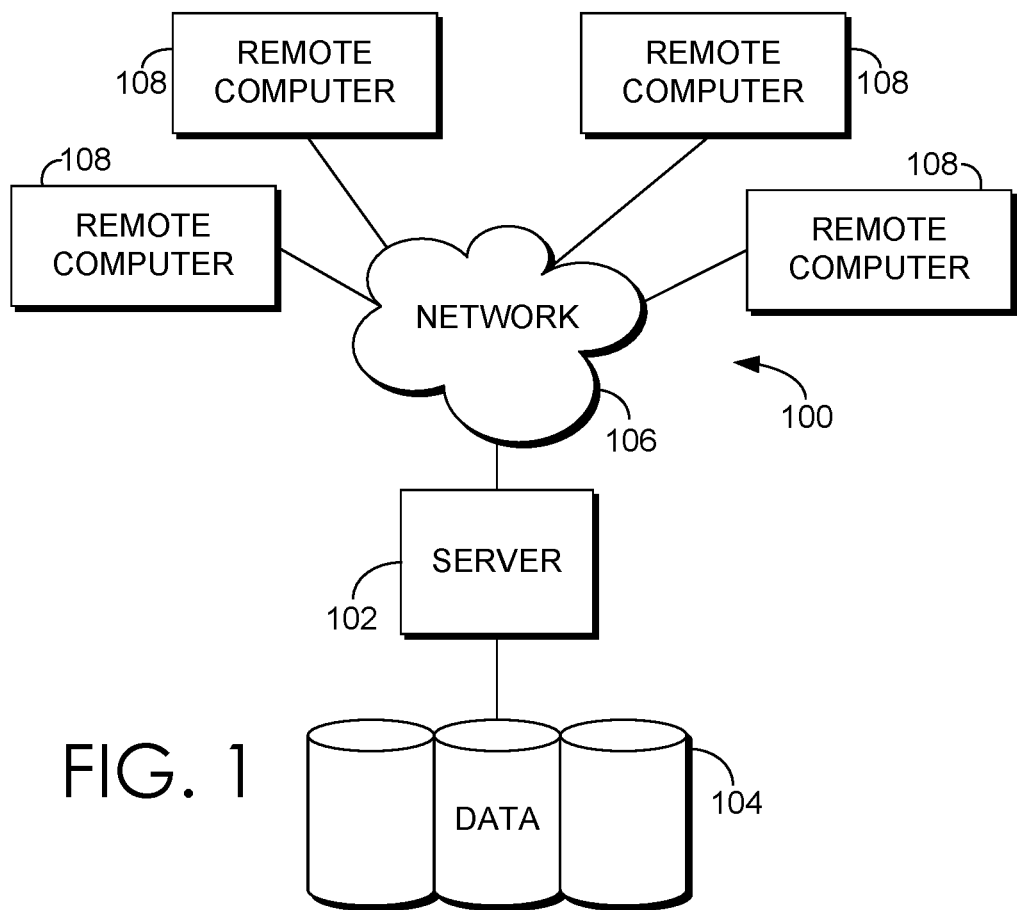
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As noted in the Background, many diseases can be passed along from one family member to another. These diseases are often due to changes or mutations in a gene that is inherited from one or both parents. However, these diseases are often misdiagnosed due to incomplete medical records or a lack of knowledge by a patient that a possible genetic disease may have been passed to the patient. As a result, the opportunity for early diagnosis and treatment may be missed and the health of the patient may deteriorate.

Embodiments of the present invention enable the identification of patients or family member having genetic disease or probable genetic disease. In particular, embodiments of the invention are directed to identifying parents, grandparents, or siblings of a patient collected during registration of the patient. If it is determined that one of the patient or the parents, grandparents, or siblings of the patient has been assigned with a diagnosis indicating a genetic disease, an alert for a genetic disease or probable genetic disease for the patient or family member of the patient is provided. The alert includes providing a genetic disease icon or or probable genetic icon in an electronic health record of the patient or family member of the patient.

In some embodiments, a clinician is prompted to confirm or rule out the patient or the parents, grandparents, or siblings of the patient having the genetic disease. Upon receiving an indication that the patient or family member has been ruled out as having the genetic disease, a record of the patient or family member in the healthcare system is updated with no alerts indicating the patient or family member does not have genetic disease or probable genetic disease. This includes removing genetic disease icon or probable genetic disease icon from the electronic health record of the patient or the family member of the patient. In contrast, upon receiving an indication that the patient or family member has been confirmed as having the genetic disease, the probable genetic disease icon is replaced with a genetic disease icon in the electronic health record of the patient or family member indicating the patient or family member has the genetic disease.

In this way, embodiments of the invention facilitate the early diagnosis and treatment of genetic diseases.

Accordingly, in one aspect, an embodiment of the present invention is directed to one or more computer storage media having computer-executable instructions embodied thereon, that when executed, perform a method for providing an indicator for genetic disease or indicator for probable genetic disease. The method comprises registering a patient in a healthcare system. The method also comprises receiving a selection of one or more family members comprising parents, grandparents, or siblings of the patient. The method further comprises determining whether any of the one or more family members has been assigned with a diagnosis indicating a genetic disease.

In another aspect of the invention, an embodiment is directed to one or more computer storage media having computer-executable instructions embodied thereon, that when executed, perform a method for providing an indicator for genetic disease or indicator for probable genetic disease. The method comprises identifying parents, grandparents, or siblings of a patient collected during registration of the patient. The method further comprises determining that one of the patient or the parents, grandparents, or siblings of the patient has been assigned with a diagnosis indicating a genetic disease. The method also comprises providing an alert for genetic disease or an alert for probable genetic disease for the patient or family member of the patient. The alert includes providing a genetic disease icon or probable genetic disease icon in an electronic health record of the patient or the family member of the patient.

In a further aspect, an embodiment is directed to a system in a healthcare computing environment that enables providing an indicator for genetic disease and indicator for probable genetic disease. The system comprises a processor; and a non-transitory computer storage medium storing computer-useable instructions that, when used by the processor, cause the processor to: identify parents, grandparents, or siblings of a patient collected during registration of the patient; determine that one of the patient or the parents, grandparents, or siblings of the patient has been assigned with a diagnosis indicating a genetic disease; provide an alert for genetic disease or alert for probable genetic disease for the patient or the family member of the patient; and prompt a clinician to confirm or rule out the patient or family member inheriting the disease.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, wearable devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, ambulatory settings, medical billing and financial offices, hospital administration settings, home healthcare environments, clinicians' offices, Center for Disease Control, Centers for Medicare & Medicaid Services, World Health Organization, any governing body either foreign or domestic, Health Information Exchange, and any healthcare/government regulatory bodies not otherwise mentioned. Clinicians may comprise a treating physician or physicians; specialists such as intensivists, surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
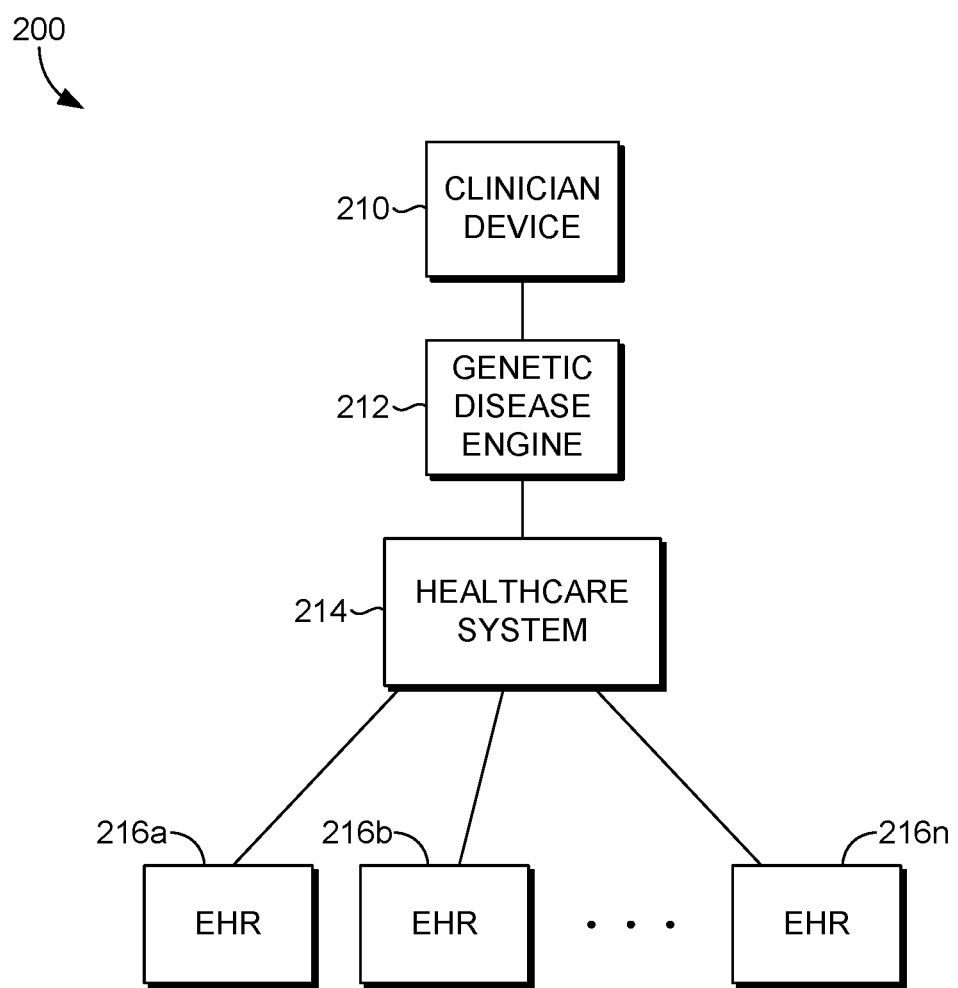
FIG. 2 is a block diagram of an exemplary system for the identification of patients having a probable inheritance of a genetic disease, in accordance with an embodiment of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a clinician device 210, a genetic disease engine 212, healthcare system 214, and electronic health record(s) (EHRs) 216a-216n, all in communication with one another via a network (not shown in FIG. 2). The network may include, without limitation, one or more secure local area networks (LANs) or wide area networks (WANs). The network may be a secure network associated with a facility such as a healthcare facility. The secure network may require that a user log in and be authenticated in order to send and/or receive information over the network.

In some embodiments, one or more of the illustrated components/modules may be implemented as stand-alone applications. In other embodiments, one or more of the illustrated components/modules may be distributed across multiple genetic disease engines. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the genetic disease engine 212 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

Each of the EHRs 216a-216n is configured to provide information to and store information communicated by, for example, the genetic disease engine 212 or healthcare system 214. The information stored in association with the EHRs 216a-216n may comprise information received from or used by various components of the genetic disease engine 212 or healthcare system 214. As illustrated in FIG. 2, it is contemplated that multiple EHRs 216a-216n may be utilized by the present invention. In this way data and context may be aggregated from multiple sources (e.g., EHRs) or multiple locations.

EHRs 216a-216n may include information corresponding to patients associated with one or more healthcare facilities. EHRs 216a-216n may comprise electronic clinical documents such as images, clinical notes, orders, summaries, reports, analyses, information received from the genetic disease engine 212, healthcare system 214, and medical devices (not shown in FIG. 2), or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information.

The content and volume of such information in the EHRs 216a-216n is not intended to limit the scope of embodiments of the present invention in any way. Further, though each EHRs 216a-216n is illustrated as a single, independent component, the EHRs 216a-216n may, in fact, include a plurality of applications and/or storage devices, for instance, a database cluster.

The clinician device 210 may be any type of computing device capable of communicating with the genetic disease engine 212 or healthcare system 214 to interact with documentation stored in the EHRs 216a-216n. Such devices may include any type of mobile and portable devices including cellular telephones, personal digital assistants, tablet PCs, smart phones, and the like.

Genetic disease engine 212 may include a processing unit, internal system memory, and a suitable system bus for coupling various system components, including one or more data stores for storing information (e.g., files and metadata associated therewith). The genetic disease engine 212 typically includes, or has access to, a variety of computer-readable media.

The computing system environment 200 is merely exemplary. While the genetic disease engine 212 is illustrated as a single unit, it will be appreciated that the genetic disease engine 212 is scalable. For example, the genetic disease engine 212 may in actuality include a plurality of computing devices in communication with one another. The single unit depictions are meant for clarity, not to limit the scope of embodiments in any form.

Initially, a clinician registers a patient in healthcare system 214, such as by using clinician device 210. In some embodiments, the patient may already be registered in healthcare system 214. The clinician may utilize the clinician device 210 to access the genetic disease engine 212 to identify parents, grandparents, or siblings of that patient. Such relationships may have been collected during registration of the patient.

The genetic disease engine 212 may determine, such as by accessing EHR(s) 216a-216n for each of the patient and/or identified relatives of the patient, that one of the patient or the parents, grandparents, or siblings of the patient has been assigned with a diagnosis indicating a genetic disease. The genetic disease engine 212 may additionally provide an alert for genetic disease or probable genetic disease for the patient or family member of the patient. The alert includes providing a genetic disease icon and/or probable genetic disease icon, such as in the EHR of the patient or family member. The probable genetic disease icon enables a clinician to quickly identify which patients may be at risk for having a genetic disease. Interaction with the probable genetic disease icon provides additional information such as information about other family members corresponding to the genetic disease (e.g., a relative name, relationship to the patient, and diagnosis). Further, the genetic disease engine 212 may prompt the clinician to confirm or rule out the patient or family member having the disease.

In some embodiments, the genetic disease engine 212 may communicate orders that assist in confirming or ruling out the patient or family member having the disease. For example, the genetic disease engine 212 may communicate with a laboratory to order a test that may confirm or rule out the patient or family member having the disease. The genetic disease engine 212 may also communicate with one or more medical devices that may provide insight into whether the patient or family member has the disease. Further, the genetic disease engine 212 may communicate an order to a pharmacy system to order a medication that may prevent or lessen the risk or symptoms of the genetic disease should the patient or family member be confirmed as having the genetic disease. Still further, the genetic disease engine 212 may communicate information regarding the genetic disease to the clinician, the patient or family member, or to others authorized to have such information.

In some embodiments, upon receiving an indication that the one or more family members was misdiagnosed with a genetic disease, the records for the patient and corresponding family members are updated in the healthcare system with no alerts. This indicates that the patient and the corresponding family members do not have a probable genetic disease.

In some embodiments, upon receiving an indication that the patient has been ruled out as having the genetic disease, the records for the patient or family member is updated in the healthcare system with no alerts. This also indicates the patient does not have a probable genetic disease. Additionally, the probable genetic disease icon is removed from the electronic health record of the patient or family member of the patient.

In some embodiments, upon receiving an indication that the patient has been confirmed as having the genetic disease, the probable genetic disease icon is replaced with a genetic disease icon in the electronic health record of the patient. This indicates the patient has the genetic disease.

Figure 3:
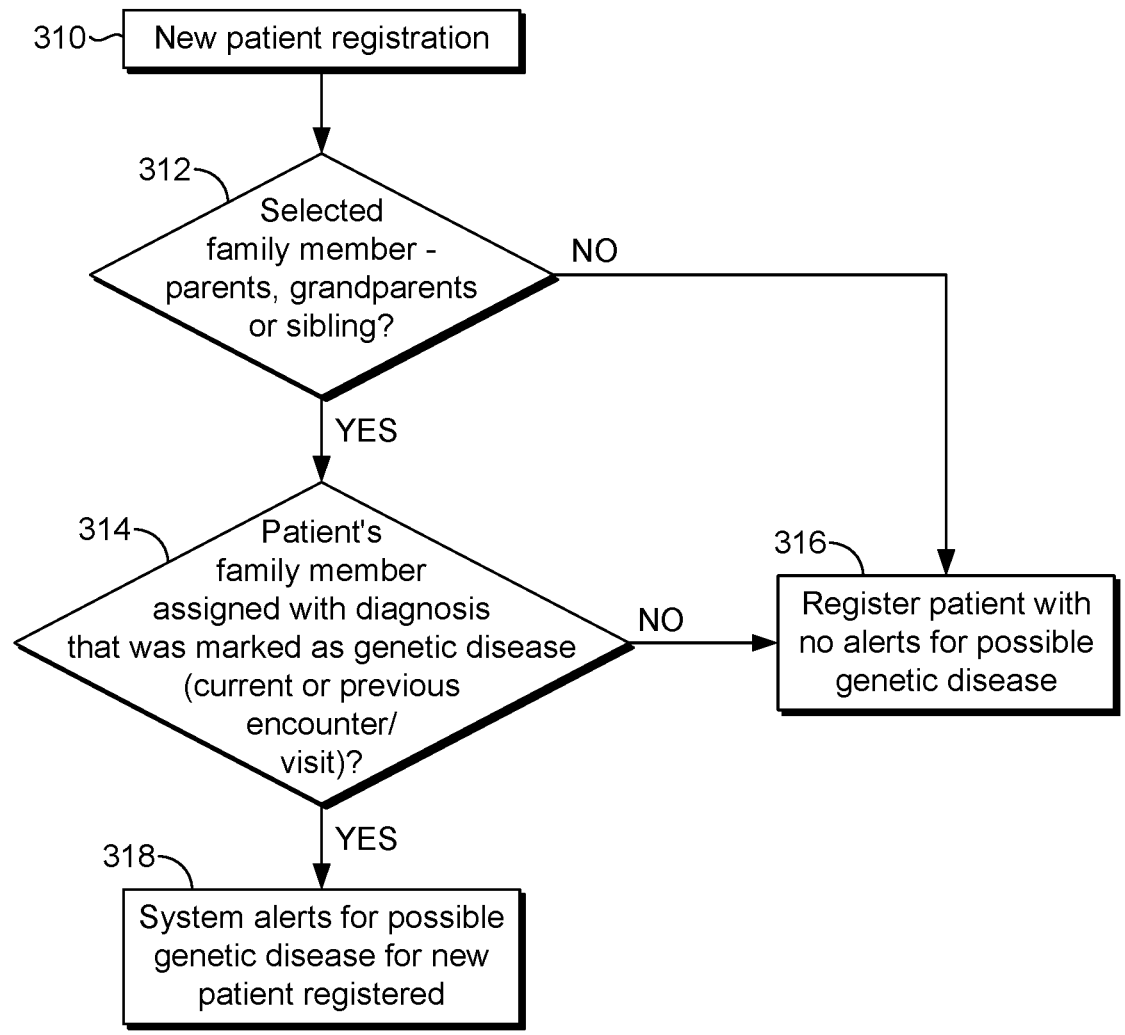
FIG. 3 is a flow diagram showing an exemplary method of identifying newly registered patients having a probable inheritance of a genetic disease, in accordance with various embodiments of the present invention.

Turning now to FIG. 3, a flow diagram is provided illustrating a method 300 of identifying patients having a probable inheritance of a genetic disease, in accordance with an embodiment of the present invention. Initially, as shown at step 310, a patient is registered in a healthcare system, such as by using by using clinician device 210 of FIG. 2.

At step 312, a selection of one or more family members comprising parents, grandparents, or siblings of the patient is received. For example, during registration, the patient may have identified one or more family members that have already been registered in healthcare system. Or, the patient may have already been identified by another family member when that family member was registered in the healthcare system. If the patient does not have any identified family members, the patient is registered in the healthcare system, at step 316, with no alerts for a possible genetic disease. This indicates the patient does not have a probable genetic disease.

At step 314, if the patient has identified family members, it is determined whether any of the family members has been assigned with a diagnosis indicating a genetic disease. In embodiments, if a family member has not been assigned with a diagnosis indication a genetic disease, the patient is registered in the healthcare system, at step 316, with no alerts for a possible genetic disease. This indicates the patient does not have a probable genetic disease.

In embodiments, if a family member has been assigned with a diagnosis indication a genetic disease, an alert is provided in the healthcare system, at step 318, indicating the patient has a probable genetic disease. The alert includes providing a probable genetic disease icon in an EHR of the patient. A genetic disease icon may be provided for the one or more family members that has previously been assigned with a diagnosis indicating a genetic disease. In some embodiments, the alert includes an option to assign the genetic disease to the patient or other family members within the healthcare system.

Also, at step 314, if the If the patient does not have any identified family members, the patient is registered in the healthcare system, at step 316, with no alerts for a possible genetic disease. This indicates the patient does not have a probable genetic disease.

If an interaction with the genetic disease icon is received, a relative name, relationship to the patient, and diagnosis may be provided. This enables the clinician how to proceed to determine how to confirm or rule out the possibility of the patient having the genetic disease. In some embodiments, the clinician is prompted to do so.

Upon receiving an indication that the one or more family members was misdiagnosed with a genetic disease, records for the patient and corresponding family members may be updated in the healthcare system with no alerts. Any related probable genetic disease icons are removed for the appropriate EHRs. This indicates the patient and the corresponding family members do not have a probable genetic disease.

In some embodiments, if an indication is received that the patient has been ruled out as having the genetic disease, the record for the patient is updated in the healthcare system with no alerts. This indicates indicating the patient does not have the genetic disease, which includes removing the probable genetic disease icon from the EHR of the patient. In contrast, in some embodiments, if an indication is received that the patient has been confirmed as having the genetic disease, the probable genetic disease icon is replaced with a genetic disease icon in the EHR of the patient indicating the patient has the genetic disease.

Figure 4:
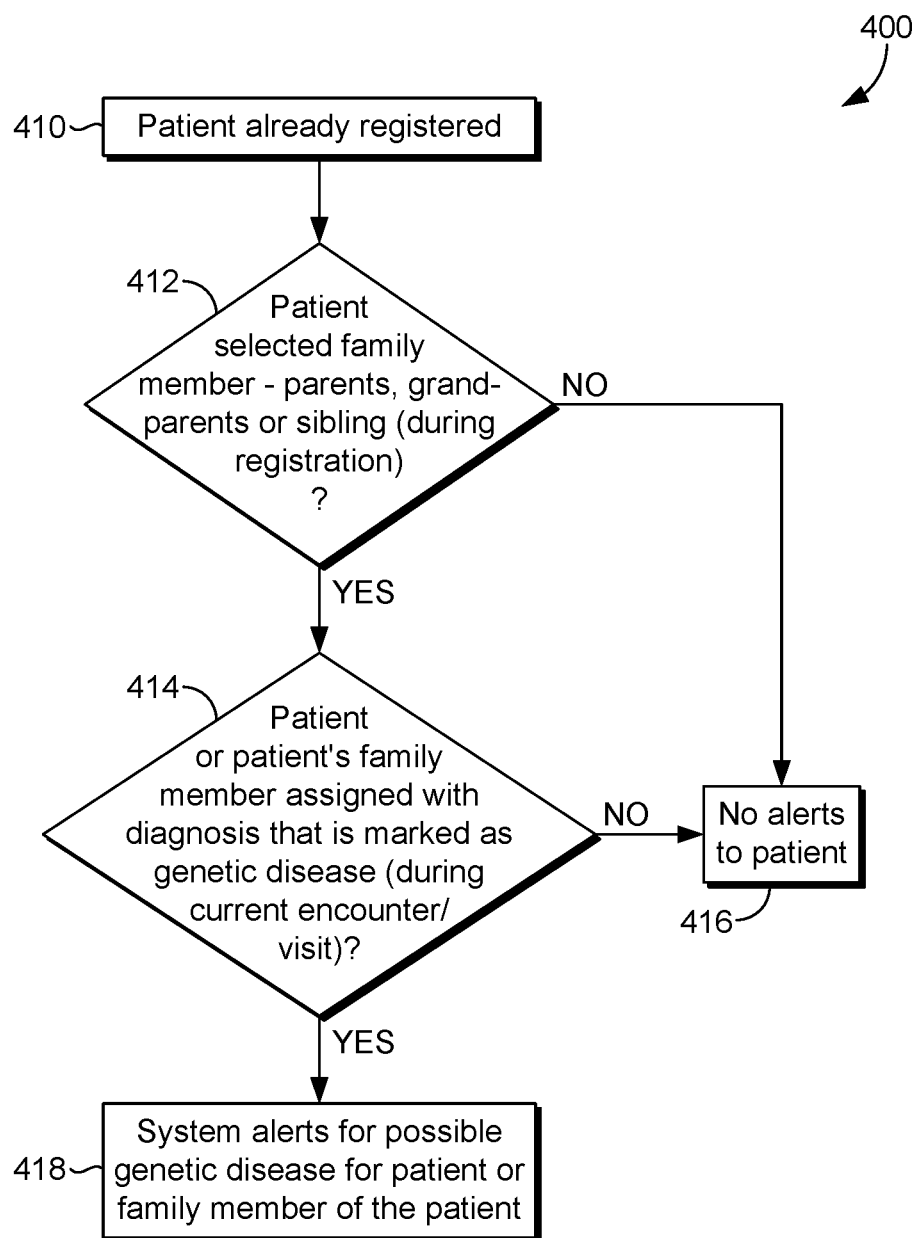
FIG. 4 is a flow diagram showing an exemplary method of identifying already registered patients having a probable inheritance of a genetic disease, in accordance with various embodiments of the present invention.
Figure 12:

Referring now to FIG. 4, a flow diagram is provided illustrating a method 400 of providing an indicator for probable inheritance of genetic disease, in accordance with an embodiment of the present invention. Initially, in some embodiments and as shown at step 410, a patient is already registered in the healthcare system. Parents, grandparents, or siblings of the patient that were collected during registration of the patient are identified, at step 412, such as by receiving a selection of the parents, grandparents, or siblings of the patient via a clinician device. If no relatives are selected, no alerts for possible genetic disease are provided, as shown at step 416.

At step 414, if it is determined that one of the patient or the parents, grandparents, or siblings of the patient has not been assigned with a diagnosis indicating a genetic disease, no alerts for possible genetic disease are provided, as shown at step 416. However, if it is determined that one of the patient or the parents, grandparents, or siblings of the patient has been assigned with a diagnosis indicating a genetic disease, an alert for possible genetic disease for the patient or family member of the patient is provided at step 418. The clinician may be prompted to confirm or rule out the patient as having the disease.

In embodiments, the alert includes an option to assign the patient or other family member as having the genetic disease within the healthcare system. For those family members that have been assigned as having the genetic disease, a genetic disease icon may be provided in their respective EHRs. When an interaction with the genetic disease icon is received, a relative name, relationship to the patient, and diagnosis is provided.

In some embodiments, if an indication is received that the patient or family member has been ruled out as having the genetic disease, a record of the patient or family member may be updated in the healthcare system with no alerts. This indicates the patient or family member does not have genetic disease or probable genetic disease and may include removing the genetic disease icon or probable genetic disease icon from the EHR of the patient or family member of the patient.

In some embodiments, if an indication is received that the patient or family member has been confirmed as having the genetic disease, the probable genetic disease icon may be replaced with a genetic disease icon in the electronic health record of the patient or family member indicating the patient or family member has the genetic disease.

Turning now to FIGS. 5-12, graphical user interfaces (GUIs) illustrating identification of patients having genetic disease and family member of the patient with probable genetic disease, in accordance with embodiments of the present invention are provided. GUI 500 enables a user to associate a diagnosis 502 (such as via clinician device 210 of FIG. 2) with a patient. If the diagnosis is a genetic disease, the genetic disease box 504 may be selected. Once these selections are saved, the system considers the diagnosis associated with the patient a genetic disease.

Figure 6:
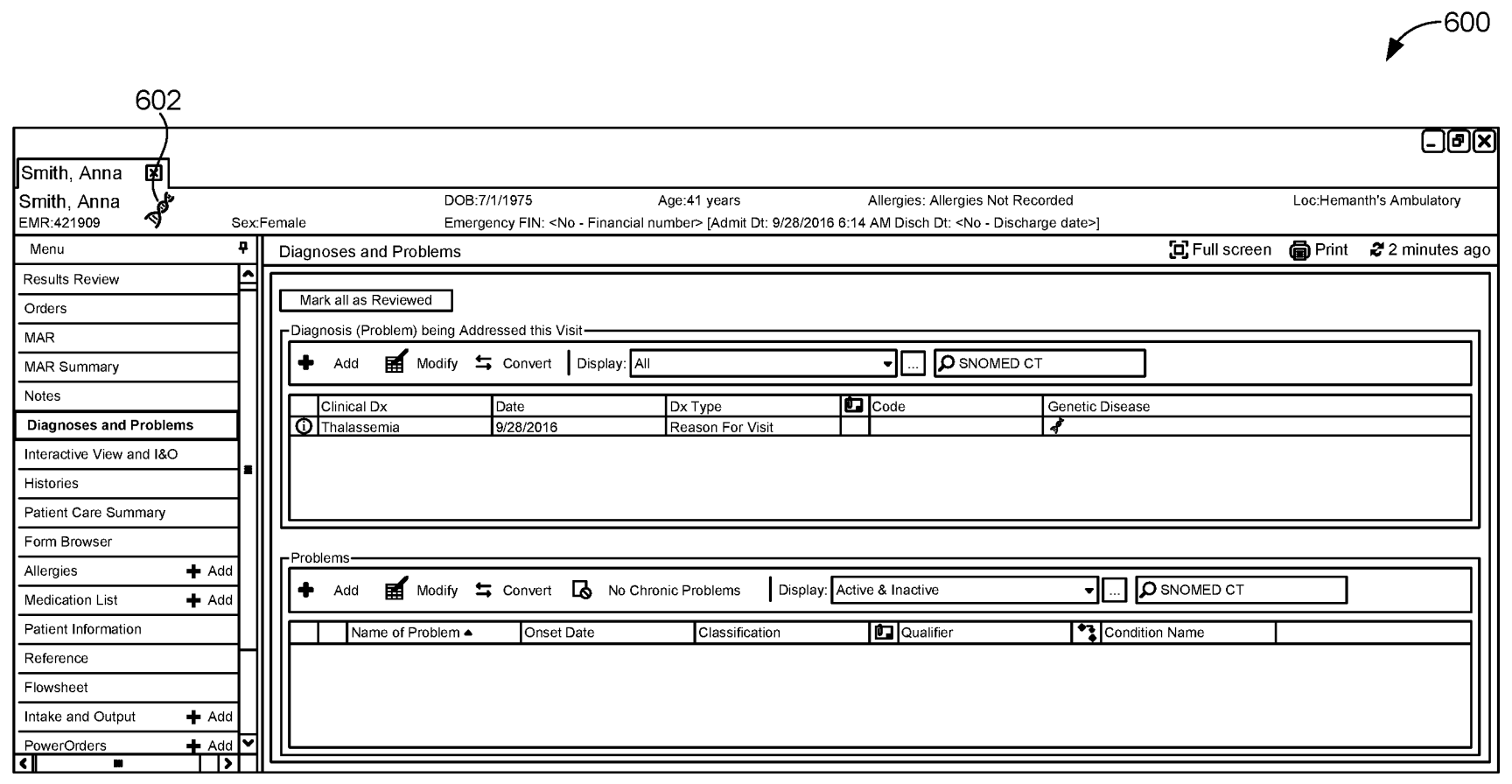
Figure 7:
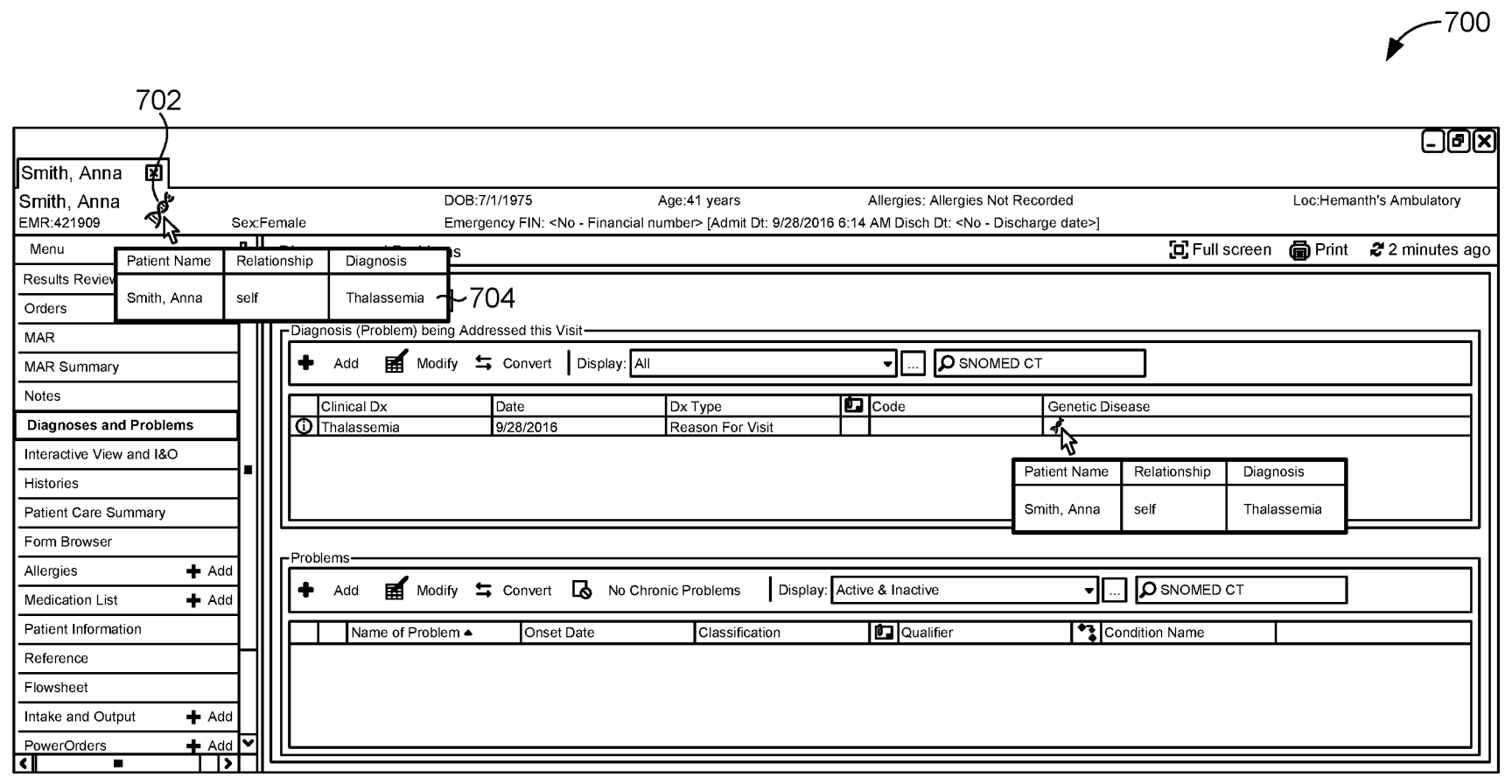

In FIG. 6, graphical user interface 600 illustrates the system providing a genetic disease icon 602 for the patient. The genetic disease icon 602 indicates that the patient has been diagnosed with a genetic disease. A new column 604 called "Genetic Disease" may also added that displays the icon for the corresponding diagnosis associated with the patient. As shown by graphical user interface 700 in FIG. 7, upon hovering over either icon 702, details 704 regarding the genetic disease are provided. For example, the details 704 may include patient name, relationship to the patient, and diagnosis.

Figure 8:
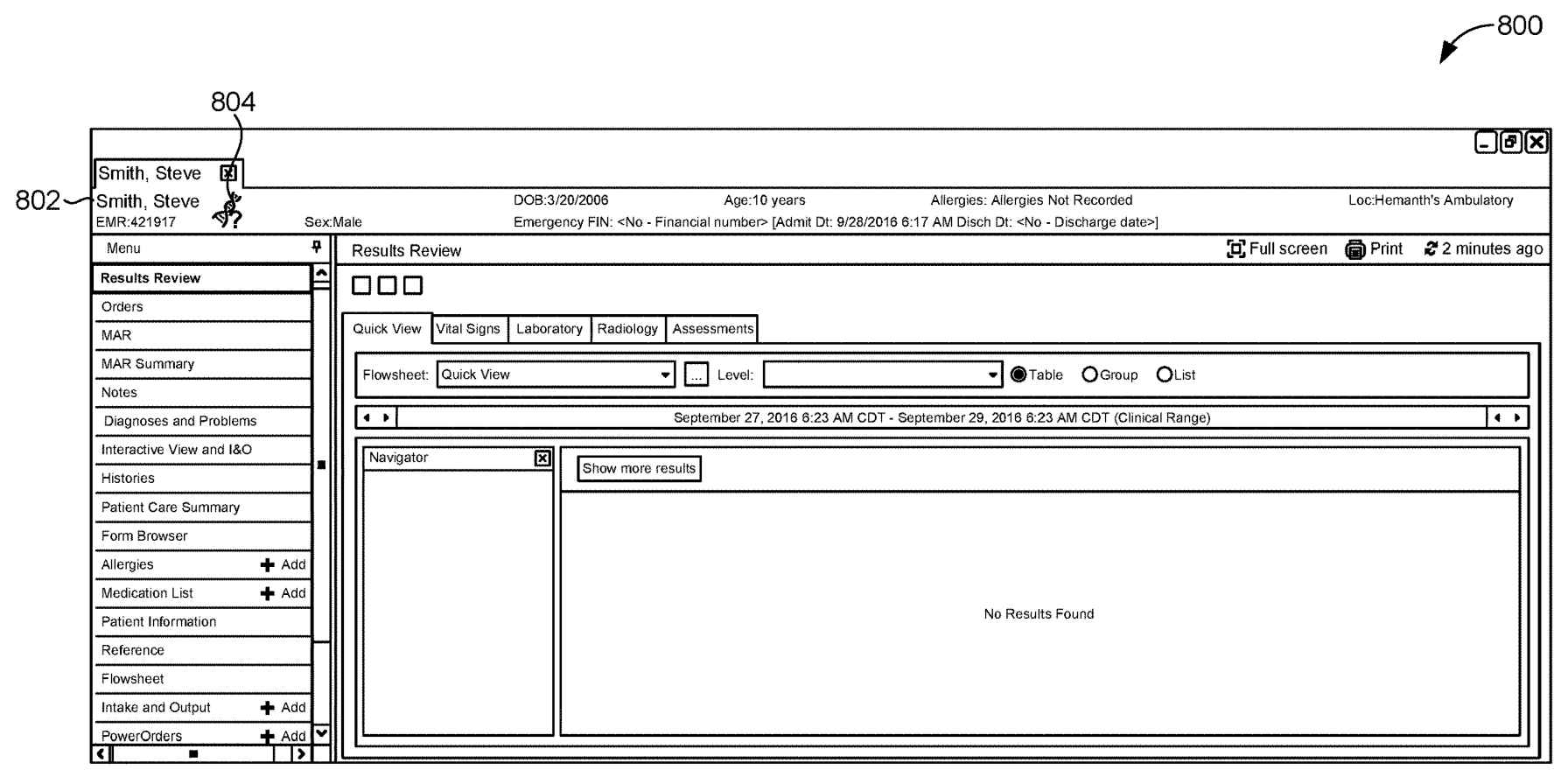

As shown in FIG. 8, graphical user interface 800 illustrates a patient 802 being registered for the first time in the healthcare system. The system determines if any relationships between the newly registered patient and existing patients are identified within the system. For example, if during registration, a relative is selected as having a relationship to the patient 802, and that relative is already associated with a diagnosis that has been marked as a genetic disease, a probable genetic disease icon 804 is displayed for patient 802. The probably genetic disease icon suggests that the patient 802 may have the possibility of inheriting the same genetic disease as the relative. This enables the clinician to take appropriate measures to confirm the diagnosis or rule out the possibility of inheriting the disease.

Figure 9:
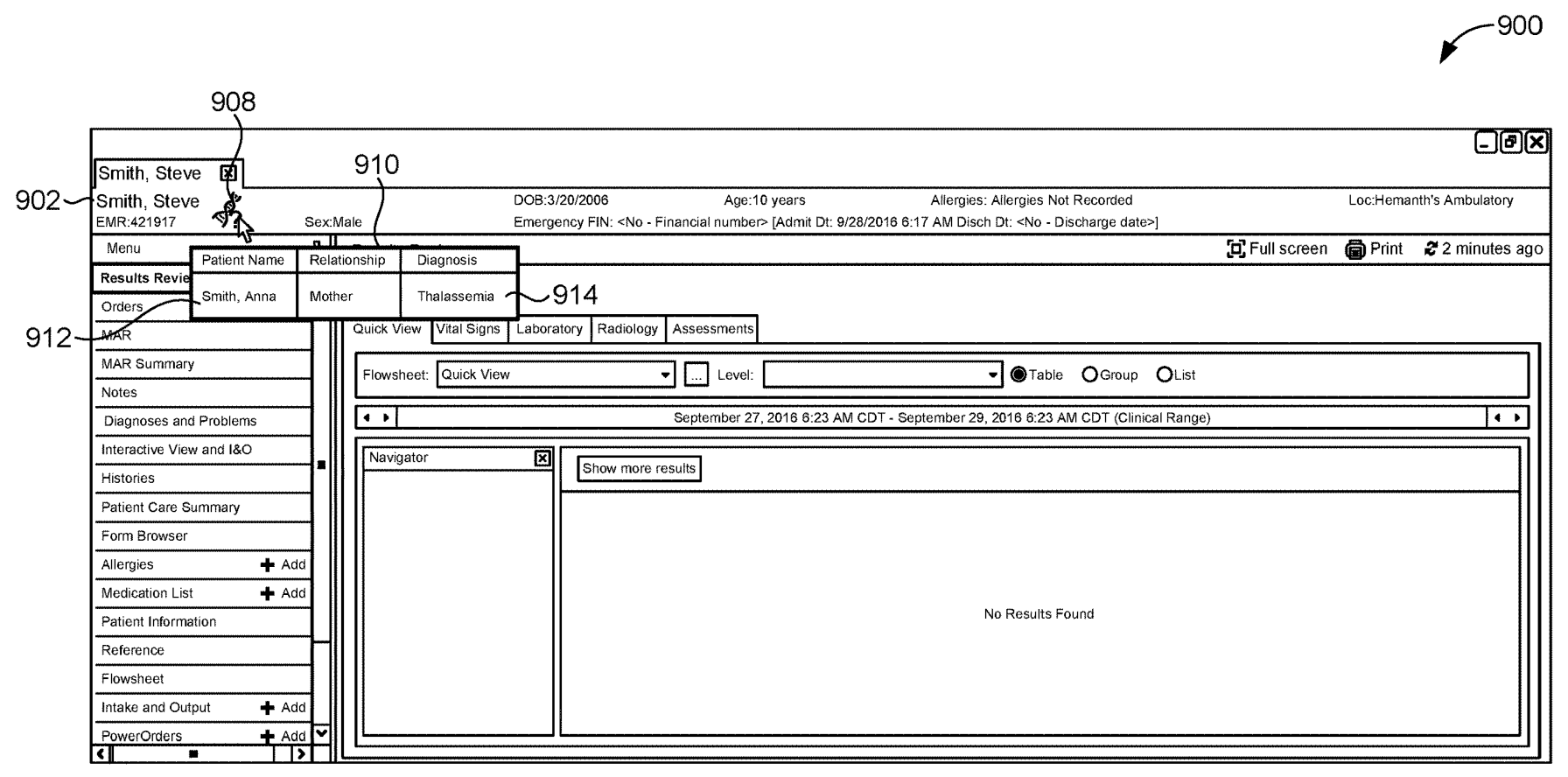

FIG. 9 depicts graphical user interface 900 illustrating a saved relationship between the newly registered patient 902 and an existent patient 912. Since the existing patient 904 is associated with a diagnosis 914 which is marked as a genetic disease, the system displays a probable genetic disease icon 908 for the newly registered patient 902. This indicates the possibility of inheriting a genetic disease. In this way, the system identifies relationships that have been established and assigns probable genetic disease icons for newly registered patients as appropriate. As shown, upon interacting with the probable genetic disease icon 908, details 910 regarding the genetic disease are provided. As illustrated, the details 910 may include patient name, relationship to the patient, and diagnosis.

Figure 10:
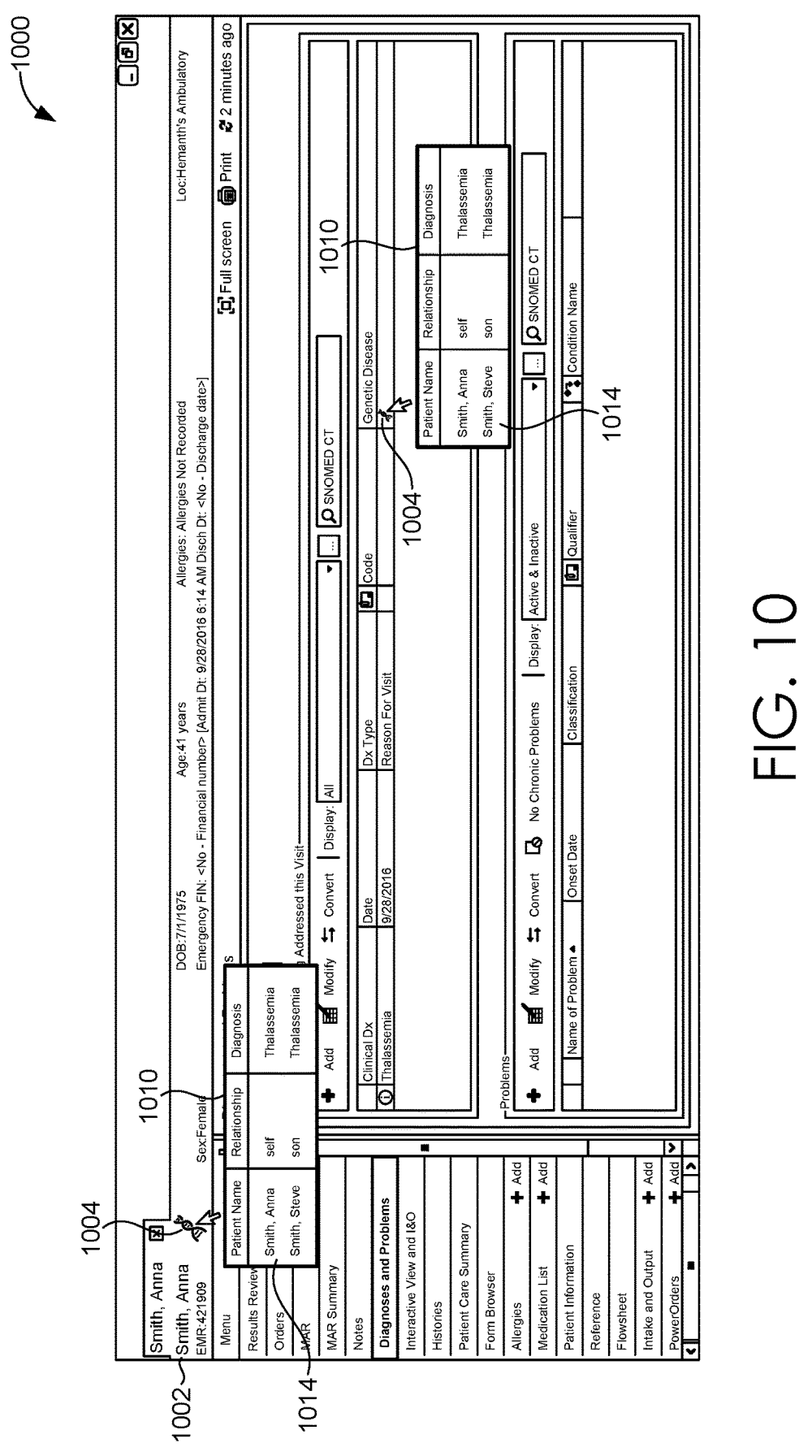

Turning now to FIG. 10, graphical user interface 1000 illustrates what happens after the newly registered patient 1014 has been identified as a relative of the patient 1002 having the genetic disease. Upon interacting with the genetic disease icon 1004, details 1010 regarding the genetic disease are provided. As illustrated, the details 1010 may include patient name, relationship to the patient, and diagnosis.

Figure 11:
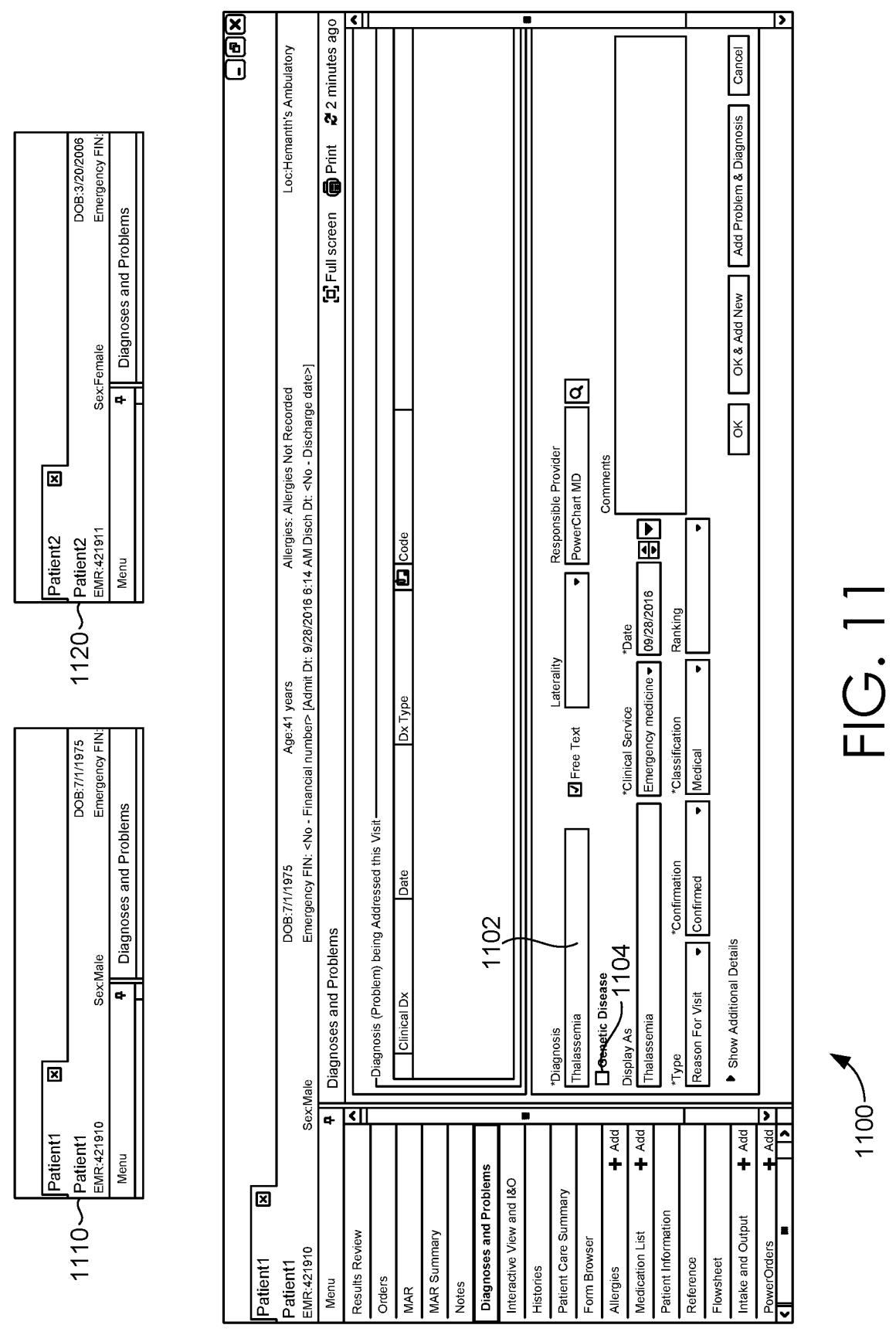

In FIG. 11, graphical user interfaces 1100, 1110, 1120 illustrates patients (i.e., Patient1 and Patient2) having an existing relationship and already being registered in the healthcare system. Based on the relationship established between Patient1 and Patient 2, the system recognizes that if one of the patients is diagnosed with a genetic disease at any point in time, the related patient will have the possibility of inheriting the genetic disease.

For example, suppose a diagnosis 1102 is added for Patient1. If that diagnosis is not marked as a genetic disease in the genetic disease box 1104, the system will not display the genetic disease icon for Patient1 or the probable genetic disease icon for Patient2. However, if at a later point in time, and referring to FIG. 12, graphical user interfaces 1200, 1210, 1220 illustrates a scenario where the clinician marks the diagnosis 1202 associated with Patient1 as a genetic disease in the genetic disease box 1204. In this case, the system displays the genetic disease icon 1212 for Patient1 and the probable genetic disease icon 1222 for Patient2. Upon interacting with the genetic disease icon 1212 or probable genetic disease icon 1222, details 1214 or details 1224 regarding the genetic disease are provided. As illustrated, the details 1214, 1224 may include patient name, relationship to the patient, and diagnosis In various embodiments, the system may correct a misdiagnosis or mistake. For example, if a diagnosis should not have marked as a genetic disease in the genetic disease box or was marked by mistake, the diagnosis can be unmarked as a genetic disease by unchecking the genetic disease box. As a result, the genetic disease icon for the patient and the probable genetic disease icon for the relative are removed upon saving the correction and no icons are provided.

As can be understood, the present invention provides systems, methods, and user interfaces for providing real-time analysis and annotation of clinical documents in a distributed system. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. Computer-readable media having computer-executable instructions embodied thereon that when executed, facilitate a method for providing an indicator for genetic disease and probable genetic disease, the method comprising:
   registering, via a clinician device, a patient in a healthcare system;
   accessing, via the clinician device, a genetic disease engine to identify parents, grandparents, or siblings, of the patient;
   receiving, at the clinician device, a selection of one or more family members of the parents, grandparents, or siblings of the patient; and
   determining, at the genetic disease engine by communicating with one or more medical devices that provide insight into whether any of the one or more family members has been assigned with a diagnosis indicating a genetic disease, whether any of the one or more family members has been assigned with the diagnosis indicating the genetic disease;
   upon determining a family member of the one or more family members has been assigned with the diagnosis indicating the genetic disease, providing, by the genetic disease engine, an alert in the healthcare system indicating the patient has a probable genetic disease, the alert including providing a probable genetic disease icon in an electronic health record of the patient;
   communicating, by the genetic disease engine, orders that assist in confirming or ruling out the patient having the disease;
   prompting a clinician, via the clinician device, to confirm or rule out the patient having the disease; and
   upon receiving an indication that the patient or family member has been confirmed as having the genetic disease, replacing the probable genetic disease icon with a genetic disease icon in the electronic health record of the patient or family member indicating the patient or family member has the genetic disease.

2. The computer-readable media of claim 1, wherein the alert includes an option to assign the genetic disease to the patient or other family members within the healthcare system.

3. The computer-readable media of claim 1, further comprising if any of the one or more family members has not been assigned with a diagnosis indicating a genetic disease, registering the patient in the healthcare system with no alerts indicating the patient does not have a probable genetic disease.

4. The computer-readable media of claim 2, further comprising providing a genetic disease icon for the one or more family members that has been assigned with a diagnosis indicating a genetic disease.

5. The computer-readable media of claim 4, further comprising receiving an interaction with the genetic disease icon.

6. The computer-readable media of claim 5, further comprising, upon receiving the interaction with the genetic disease icon, providing a relative name, relationship to the patient, and diagnosis.

7. The computer-readable media of claim 1, further comprising providing a probable genetic disease icon for the patient who has one or more family members assigned with a diagnosis indicating a genetic disease.

8. The computer-readable media of claim 7, further comprising receiving an interaction with the probable genetic disease icon.

9. The computer-readable media of claim 8, further comprising, upon receiving the interaction with the probable genetic disease icon, providing a relative name, relationship to the patient, and diagnosis.

10. The computer-readable media of claim 1, further comprising, upon receiving an indication that the one or more family members was misdiagnosed with a genetic disease, updating a record for the patient and corresponding family members in the healthcare system with no alerts indicating the patient does not have a probable genetic disease and the corresponding family members do not have the genetic disease.

11. The computer-readable media of claim 1, further comprising, upon receiving an indication that the patient has been ruled out as having the genetic disease, updating a record of the patient in the healthcare system with no alerts indicating the patient does not have a probable genetic disease, including removing the probable genetic disease icon from the electronic health record of the patient.

12. A method for providing an indicator for probable inheritance of genetic disease, the method comprising:

identifying, by a genetic disease engine, parents, grandparents, or siblings of a patient collected during registration of the patient at a clinician device;

determining, at the genetic disease engine by communicating with one or more medical devices that provide insight into whether the patient, the parents, grandparents, or siblings of the patient been assigned with a diagnosis indicating a genetic disease, that one of the patient or the parents, grandparents, or siblings of the patient has been assigned with the diagnosis indicating the genetic disease; and upon determining that one of the patient or the parents, grandparents, or siblings of the patient has been assigned with the diagnosis indicating the genetic disease, providing, by the genetic disease engine, an alert for genetic disease or probable genetic disease for the patient or family member of the patient, the alert including providing a genetic disease icon or probable genetic disease icon in an electronic health record of the patient or family member of the patient;

communicating, by the genetic disease engine, orders that assist in confirming or ruling out the patient having the disease;

prompting a clinician, via the clinician device, to confirm or rule out the patient having the disease; and upon receiving an indication that the patient or family member has been confirmed as having the genetic disease, replacing the probable genetic disease icon with a genetic disease icon in the electronic health record of the patient or family member indicating the patient or family member has the genetic disease.

13. The method of claim 12, wherein the alert includes an option to assign the genetic disease to the patient or other family members within the healthcare system.

14. The method of claim 13, further comprising providing a genetic disease icon for the one or more family members that has been assigned with a genetic disease.

15. The method of claim 14, further comprising receiving an interaction with the genetic disease icon.

16. The method of claim 15, further comprising, upon receiving the interaction with the genetic disease icon, providing a relative name, relationship to the patient, and diagnosis.

17. The method of claim 12, further comprising providing a probable genetic disease icon for patient who has one or more family members assigned with a diagnosis indicating a genetic disease.

18. The method of claim 17, further comprising receiving an interaction with the probable genetic disease icon.

19. The method of claim 18, further comprising, upon receiving the interaction with the probable genetic disease icon, providing a relative name, relationship to the patient, and diagnosis.

20. The method of claim 12, further comprising, upon receiving an indication that the patient or family member has been ruled out as having the genetic disease, updating a record of the patient or family member in the healthcare system with no alerts indicating the patient or family member does not have genetic disease or probable genetic disease, including removing the genetic disease icon or probable genetic disease icon from the electronic health record of the patient or family member of the patient.

21. A system in a healthcare computing environment comprising:

a processor; and a non-transitory computer storage medium storing computer-useable instructions that, when used by the processor, causes the processor to:

access, via a clinician device, a genetic disease engine to identify parents, grandparents, or siblings of a patient collected during registration of the patient;

determine, at the genetic disease engine by communicating with one or more medical devices that provide insight into whether the patient, the parents, grandparents, or siblings of the patient has been assigned with a diagnosis indicating a genetic disease, that one of the patient or the parents, grandparents, or siblings of the patient has been assigned with the diagnosis indicating the genetic disease;

upon determining a family member of the one or more family members has been assigned with the diagnosis indicating the genetic disease, provide, by the genetic disease engine, an alert for genetic disease or probable genetic disease for the patient or family member of the patient;

communicate, by the genetic disease engine, orders that assist in confirming or ruling out the patient having the disease;

prompt a clinician to confirm or rule out the patient or family member having the disease; and upon receiving an indication that the patient or family member has been confirmed as having the genetic disease, replacing the probable genetic disease icon with a genetic disease icon in the electronic health record of the patient or family member indicating the patient or family member has the genetic disease.

* * * * *

UNITED STATES PATENT AND TRADEMARK OFFICE
CERTIFICATE OF CORRECTION

Page 1 of 1

PATENT NO. : 10,910,108 B2
APPLICATION NO. : 15/393817
DATED : February 2, 2021
INVENTOR(S) : Soumen Tapadar et al.

It is certified that error appears in the above-identified patent and that said Letters Patent is hereby corrected as shown below:

On the Title Page

Column 02, (74) Attorney, Agent, or Firm: Please remove "Bacon, L.L.P." and replace with --Bacon L.L.P.--.

In the Specification

Column 02, Line 43: Please remove "or or" and replace with --or--.

Column 11, Line 21: Please remove "diagnosis" and replace with --diagnosis.--.

In the Claims

Column 13, Line 07 Claim 12: After "patient" please insert --has--.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*